United States Patent [19]

St. Georgiev et al.

[11] 4,276,292

[45] Jun. 30, 1981

[54] TRIAZOLOBENZOXAZIN-4-ONES

[75] Inventors: Vasil St. Georgiev, New Rochelle; Bernard Loev, Scarsdale; Robert Mack, Valley Stream; John Musser, Hawthorne, all of N.Y.

[73] Assignee: USV Pharmaceutical Corporation, Tuckahoe, N.Y.

[21] Appl. No.: 149,080

[22] Filed: May 12, 1980 (Under 37 CFR 1.47)

[51] Int. Cl.$^3$ .................. A61K 31/535; C07D 498/04
[52] U.S. Cl. ............................. 424/248.4; 424/248.5; 424/248.53; 424/248.55; 544/101; 544/105
[58] Field of Search ..................... 544/101; 424/248.4, 424/248.5, 248.53

[56] References Cited

U.S. PATENT DOCUMENTS 3,929,783  12/1975  Krapcho et al. .................. 544/101 X Primary Examiner—John D. Randolph
Attorney, Agent, or Firm—Ernest B. Lipscomb, III

[57] ABSTRACT

New triazolobenzoxazinones are described as well as the use thereof as anti-allergenic agents.

11 Claims, No Drawings

TRIAZOLOBENZOXAZIN-4-ONES

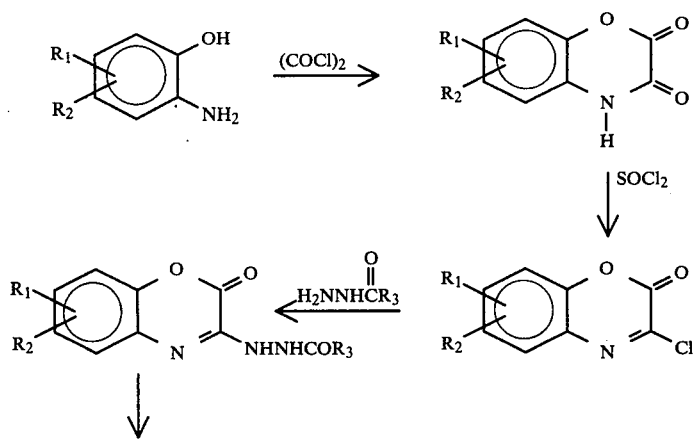

This invention relates to certain new triazolobenzoxazin-4-ones possessing useful anti-allergic activity which are particularly useful in the treatment of asthma.

The triazolobenzoxazin-4-ones of this invention are new compounds not previously described in the literature and show significant anti-allergic activity as shown in the standard tests used for evaluation of such activity.

The new triazolobenzoxazinones of this invention are of the following formula:

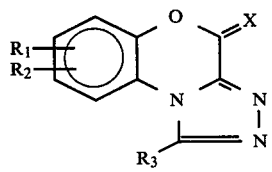

wherein,

X is S or O;

each of $R_1$ and $R_2$ is hydrogen, alkyl, alkenyl, alkynyl, cycloalkyl, aryl, aralkyl, sulfonamido, halogen, alkoxy, alkenyloxy, alkynyloxy, cyano, hydroxy, acyloxy, nitro, amino, alkylamino, alkanoylamino, carbalkoxyamino, methanesulfonyl, carboxy, carbalkoxy or trihalomethyl, or taken together, methylenedioxy;

$R_3$ is hydrogen, hydroxy, alkyl, alkenyl, alkynyl, aryl, acyl, aralkyl, cycloalkyl, or carbalkoxy; and acid addition salts thereof. The total number of carbon atoms in each such hydrocarbyl substituent can range up to about 10.

The preferred compounds are those in which the hydrocarbyl radicals contain up to about 7 carbon atoms when aliphatic and up to 10 carbon atoms when aromatic, e.g., phenyl, tolyl and naphthyl.

The particularly preferred compounds of the invention are those in which X is oxygen, that is, the triazolobenzoxazinones.

The new compounds of the invention can be prepared by art-recognized procedures from known starting compounds. For example, the following procedure can be employed wherein $R_1$, $R_2$ and $R_3$ are as previously defined with the exception that in these intermediates, $R_3$ cannot be hydroxy.

FORMULA I

Substituents $R_1$ to $R_3$ can be added after formation of the basic ring structures by known substitution reactions, or conversion of substituents such as reduction of nitro to form amino. The substitution reactions mentioned include, for example, alkylation and acylation by known procedures.

Substituents on the present new compounds which are reactive and could interfere with ring closure reactions are best introduced by subsequent reactions known to the art such as reduction of nitro to amino, or hydrolysis of cyano to carboxamide or carboxy groups; alternatively, such reactive groups can be protected as by, for example, acylation of an amino group, followed by hydrolysis after ring closure.

Using the procedures described, a wide variety of heterocyclic compounds can be prepared, as follows:

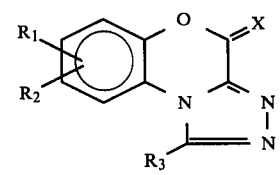

| $R_1$ | $R_2$ | X | $R_3$ |
|---|---|---|---|
| H | H | O | COCH₃ |
| CH₃ | H | O | n-C₃H₇ |
| CH₃ | CH₃ | O | i-C₃H₇ |
| Cl | H | S | C₆H₅ |
| OCH₃ | H | O | C₆H₅CH₂— |
| C₆H₅ | H | O | CH₃C₆H₄ |
| CF₃ | CH₃ | O | C₃H₇CO |
| OC₃H₅ | H | S | COOCH₃ |
| OC₆H₅ | H | O | C₄H₉CO |
| H | H | O | H |
| OH | CH₃ | O | H |
| C₄H₉ | OH | O | H |
| CH₂OH | H | O | C₄H₇ |
| NH₂ | OCH₃ | O | C₄H₉ |
| NHCH₃ | H | O | H |
| SH | H | O | H |
| SC₃H₇ | H | O | H |
| C₄H₇ | OCH₃ | O | H |
| NO₂ | H | O | CH₃CO |
| C₆H₅CH₂O | H | O | CH₃ |
| OCF₃ | H | O | CH₃CO |

| R₁ | R₂ | X | R₃ |
|---|---|---|---|
| C₂H₄NH₂ | H | O | H |
| H | H | O | H |
| H | H | O | H |
| H | H | O | H |

The present new heterocyclic compounds are therapeutically useful as such or can be employed in the form of salts in view of their basic nature. Thus, these compounds form salts with a wide variety of acids, inorganic and organic, including therapeutically-acceptable acids. The salts with therapeutically-acceptable acids are, of course, useful in the preparation of formulations where water solubility is desired. The salts with therapeutically-unacceptable acids are particularly useful in the isolation and purification of the present new compounds. Therefore, all acid salts of the present new compounds are contemplated by the present invention.

The pharmaceutically-acceptable acid addition salts are of particular value in therapy. These include salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, succinic, arylsulfonic, e.g., p-toluenesulfonic acids, and the like. The pharmaceutically-unacceptable acid addition salts, while not useful for therapy, are valuable for isolation and purification of the new substrates. Further, they are useful for the preparation of pharmaceutically-acceptable salts. Of this group, the more common salts include those formed with hydrofluoric and perchloric acids. Hydrofluoride salts are particularly useful for the preparation of the pharmaceutically-acceptable salts, e.g., the hydrochlorides, by solution in hydrochloric acid and crystallization of the hydrochloride salt formed. The perchloric acid salts are useful for purification and crystallization of the new products.

As therapeutic agents, the present new heterocyclic compounds are particularly useful as anti-allergic agents, acting via inhibition of mediator release. Although the compounds are not active in the passive cutaneous anaphylaxis (PCA) screen, they do inhibit histamine release from passively sensitized rat mast cells.

The therapeutic agents of this invention may be administered alone or in combination with pharmaceutically-acceptable carriers, the proportion of which is determined by the solubility and chemical nature of the compound, chosen route of administration and standard pharmaceutical practice. For example, they may be administered orally in the form of tablets or capsules containing such excipients as starch, milk sugar, certain types of clay and so forth. They may be administered orally in the form of solutions which may contain coloring and flavoring agents or they may be injected parenterally, that is, intramuscularly, intravenously or subcutaneously. For parenteral administration, they may be used in the form of a sterile solution containing other solutes, for example, enough saline or glucose to make the solution isotonic.

The physician will determine the dosage of the present therapeutic agents which will be most suitable and it will vary with the form of administration and the particular compound chosen, and furthermore, it will vary with the particular patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of an active agent will be required to produce the same effect as a smaller quantity given parenterally. The compounds are useful in the same manner as other anti-allergy agents and the dosage level is of the same order of magnitude as is generally employed with these other therapeutic agents. The therapeutic dosage will generally be from 10 to 750 milligrams per day and higher although it may be administered in several different dosage units. Tablets containing from 10 to 250 mg. of active agent are particularly useful.

The following examples further illustrate the invention.

EXAMPLE 1

(I) 4H-(1,2,4)Triazolo(3,4-c)(1,4)benzoxazine-4-one.

To a hot solution of 2.32 g. (0.0386 mole) of formyl hydrazine in 50 ml. of 1,2-dimethoxyethane was added over 2 minutes to a solution of 7.0 g. (0.0386 mole) of 3-chloro-1,4-benzoxazine-2-one in 90 ml. of dimethoxyethane. The mixture was refluxed for 18 hours, the yellow precipitate was filtered and recrystallized from 1,2-dimethoxyethanol to give pure product of m.p. 270°–275°.

In the same way as above, using appropriate starting materials, the following products were prepared:
(II) 7-Methyl-4H-(1,2,4)triazolo(3,4-c)(1,4)benzoxazine-4-one, m.p. 273°–275°.
(III) 1,7-Dimethyl-4H-(1,2,4)triazolo(3,4-c)(1,4)benzoxazine-4-one, m.p. 258°–261°.
(IV) 8-Chloro-4H-(1,2,4)triazolo(3,4-c)(1,4)benzoxazine-4-one, m.p. >300°.
(V) 1-Methyl-4H-(1,2,4)triazolo(3,4-c)(1,4)benzoxazine-4-one, m.p. 302°–305°.

In the same way as above using ethyl carbazate as starting material, there was prepared
(VI) 1-hydroxy-8-methyl-4H-(1,2,4)triazolo(3,4-c)(1,4)benzoxazine-4-one, m.p. 290°–300°.

EXAMPLE 2

4H(1,2,4)triazolo(3,4-c)(1,4-benzothiazine-4-one.

In the same was as described in Example 1, reaction of formyl hydrazine and 3-chloro-1,4-benzothiazine-2-one gave the title compound, m.p. 288°–292° after recrystallization from acetonitrile.

Each of the products of Example 1 were found to inhibit histamine release from passively sensitized rat mast cells according to the procedure described by Kusner, et al., Journal of Pharmacology and Experimental Therapeutics, 184, 41 (1973). In identical test, the Example 2 compound was inactive.

What is claimed is:
1. An anti-allergic compound of the formula:

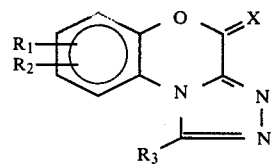

wherein,
X is S or O;

each of $R_1$ and $R_2$ is hydrogen, alkyl, alkenyl, alkynyl, cycloalkyl, aryl, aralkyl, sulfonamido, halogen, alkoxy, alkenyloxy, alkynyloxy, cyano, hydroxy, acyloxy, nitro, amino, alkylamino, alkanoylamino, carbalkoxyamino, methanesulfonyl, carboxy, carbalkoxy or trihalomethyl, or taken together, methylenedioxy;

$R_3$ is hydrogen, hydroxy, alkyl, alkenyl, alkynyl, aryl, acyl, aralkyl, cycloalkyl, or carbalkoxy; and acid addition salts thereof.

2. 4H-(1,2,4)Triazolo(3,4-c)(1,4)benzoxazine-4-one.

3. 7-Methyl-4H-(1,2,4)triazolo(3,4-c)(1,4)benzoxazine-4-one.

4. 1,7-Dimethyl-4H-(1,2,4)triazolo(3,4-c)(1,4)benzoxazine-4-one.

5. 8-Chloro-4H-(1,2,4)triazolo(3,4-c)(1,4)benzoxazine-4-one.

6. 1-Methyl-4H-(1,2,4)triazolo(3,4-c)(1,4)benzoxazine-4-one.

7. 1-Hydroxy-8-methyl-4H(1,2,4)triazolo(3,4-c)(1,4)benzoxazine-4-one.

8. A therapeutic composition comprising a compound according to claim 1.

9. The composition according to claim 8 wherein said compound is 1-methyl-4H-(1,2,4)triazolo(3,4-c)(1,4)benzoxazine-4-one.

10. The composition according to claim 8 wherein said compound is 7-methyl-4H-(1,2,4)triazolo(3,4-c)(1,4)benzoxazine-4-one.

11. The composition according to claim 8 wherein said compound is 8-chloro-4H-(1,2,4)triazolo(3,4-c)(1,4)benzoxazine-4-one.

* * * * *